US00PP16936P2

(12) United States Plant Patent
Kordes

(10) Patent No.: US PP16,936 P2
(45) Date of Patent: Aug. 1, 2006

(54) CLIMBING ROSE PLANT NAMED 'KORADIGEL'

(50) Latin Name: *Rosa hybrida*
Varietal Denomination: KORadigel

(75) Inventor: Tim-Hermann Kordes, Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 11/071,748

(22) Filed: Mar. 2, 2005

(51) Int. Cl.
*A01H 5/00* (2006.01)

(52) U.S. Cl. ..... Plt./114

(58) Field of Classification Search ..... Plt./114, Plt./115
See application file for complete search history.

(56) References Cited

PUBLICATIONS

Gemman PBR Application RO8 2448 Apr. 5, 2004 W. Kordes' Söhne.
QZ (CPVO) Application 20041555 Aug. 19, 2004 W. Kordes' Söhne.

*Primary Examiner*—Kent Bell
*Assistant Examiner*—June Hwu

(57) ABSTRACT

A new and distinct variety of rose with abundant, novel pink flowers, and attractive foliage with very good disease resistance. It exhibits vigorous growth and an upright climbing habit. The new variety propagates well from traditional methods. This new and distinct variety has shown to be uniform and stable in the resulting generations from asexual propagation.

1 Drawing Sheet

CROSS REFERENCES AND FEDERAL R&D STATEMENT

There are no cross referenced or related applications. This variety was developed without the aid of any research grant.

Latin name of genus and species: The botanical classification of the new rose plant is *Rosa hybrida.*

Variety denomination: The denomination of the new variety is 'KORadigel'.

BACKGROUND OF THE INVENTION

The new variety of rose plant of the present invention originated from a controlled crossing in a breeding program of two distinct parents during the summer of 1994. The crossing was between an un-named seedling and an un-named seedling.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORadigel'.

SUMMARY OF THE INVENTION

The new rose plant may be distinguished from its seed parent, an un-named seedling whose parents were La Sevillana and Sympathie, by the following combination of characteristics:

1. 'KORadigel' has pink flowers while the seed parent has red flowers, and
2. the flowers of 'KORadigel' have more petals and stronger fragrance.

The new rose plant may be distinguished from its pollen parent, an un-named seedling by the following combination of characteristics:

1. 'KORadigel' has pink flowers while the pollen parent has yellow flowers, and
2. the flowers of 'KORadigel' have more petals and stronger fragrance.

The objective of the hybridization was to create a new and distinct rose plant with unique qualities, such as:

1. Vigorous, upright growth with long arching canes;
2. Abundant attractive, recurrent flowers;
3. Attractive and abundant foliage, and;
4. Resistance to diseases encountered in landscapes and gardens.

This combination of qualities is not present in prior rose varieties. These objectives have been substantially achieved and in that distinguish 'KORadigel' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORadigel' was selected in May, 1995 from the seedling beds to be asexually propagated for further evaluation. The first asexual propagation of 'KORadigel' was done by budding to seedling understocks in July, 1995 at the W. Kordes Söhne Nursery in Offenseth-Sparrieshoop, Germany.

This initial and other subsequent propagations conducted in controlled environments show that the foregoing and all other characteristics of 'KORadigel' come true to form and are transmitted through succeeding generations.

BRIEF DESCRIPTION OF THE DRAWING

The accompanying color illustration, labeled as SHEET 1, shows as true as is reasonably possible to obtain in color photographs of this type, the typical characteristics of open flowers of 'KORadigel'.

DETAILED BOTANICAL DESCRIPTION

The following is a description of 'KORadigel', as observed in its growth in a nursery in Sparrieshoop, Germany on plants of 2 years of age. Color references are made using The Royal Horticultural Society (London, England) Colour Chart, 2001 except where common terms of color are used.

For a comparison, several physical characteristics of the rose variety 'KORtersen', a non-patented rose variety from the same inventor are compared to 'KORadigel' in Chart 1.

CHART 1

| Characteristic: | 'KORadigel' | 'KORtersen' |
|---|---|---|
| Flower color | Red-Purple Group N66B | Red Group 37C. |
| Petals | 45–55 petals. | 80–100 petals. |

Parents:

*Seed parent.*—Un-named seedling.

*Pollen parent.*—Un-named seedling.

Classification:

*Botanical classification.*—*Rosa hybrida,* 'KORadigel'.

*Commercial classification.*—Climbing rose.

FLOWER AND FLOWER BUD

Blooming habit: Recurrent flowering.

Flower bud:

*Size.*—Upon opening, 30–40 mm in length from base of receptacle to end of bud.

*Bud form.*—Pointed ovoid to ovoid.

*Bud color.*—As sepals first unfold, bud color is Red-Purple Group 58A. When ¼ open, the upper surface of petals is Red-Purple Group N66A, and the lower surface is Red-Purple Group N66A.

*Sepals.*—Size: Relatively small and short. Average 12 mm long×6 mm wide. Shape: Weak foliaceous appendages on three of the five sepals. Sepal apex is cirrose. Base is flat at union with receptacle. Quantity: Five. Surface texture: Upper and lower surfaces with limited pubescence. Limited numbers of stipitate glands are present. Color: Upper surface Green Group 138A. Lower surface Green Group 138A.

Receptacle:

*Surface.*—Nearly smooth, with some fine hairs.

*Color.*—Green Group 138A.

*Shape.*—Funnel.

*Size.*—6 mm (h)×8 mm (w).

Peduncle:

*Surface.*—Near smooth with some stipitate glands.

*Length.*—40–60 mm average length.

*Diameter.*—2.0–3.0 mm average diameter.

*Color.*—Green Group 138A with intonations of Red-Purple Group 183C.

*Strength.*—Strong.

*Borne.*—Multiple flower buds per stem, generally 6 to 8.

Flower bloom:

*Fragrance.*—Strong, with tones of fruit and spice.

*Duration.*—On the plant 3–5 days. Senesced petals drop away cleanly.

*Size.*—Medium flowered garden rose. Average flower diameter is 65–75 mm when open.

*Form.*—Shape of flower when viewed from the side: Upon opening, upper part: Flattened convex. Upon opening, lower part: Flattened convex. Open flower, upper part: Flat to flattened convex. Open flower, lower part: Flat to flattened convex.

Color:

*Upon opening, petals.*—Outermost petals: Outer Side: Red-Purple Group 67A. Inner Side: Red-Purple Group N66B. Innermost petals: Outer Side: Red-Purple Group 67A. Inner Side: Red-Purple Group N66B.

*Upon opening, basal petal spots.*—Basal petal spot, outermost petals: Outer Side: White Group 155C. Inner Side: White Group 155C. Basal petal spot, innermost petals: Outer Side: White Group 155C. Inner Side: White Group 155C.

*After opening, petals.*—Outermost petals: Outermost petals: Outer Side: Red-Purple Group 67B. Inner Side: Red-Purple Group N66C. Innermost petals: Outer Side: Red-Purple Group 67B. Inner Side: Red-Purple Group N55C.

*After opening, basal petal spots.*—Basal petal spot, outermost petals: Outer Side: White Group 155C. Inner Side: White Group 155C. Basal petal spot, innermost petals: Outer Side: White Group 155C. Inner Side: White Group 155C. Variegations: White coloration may extend up center of outer side of petal to as much as 25% of petal length, primarily on innermost petals.

General tonality: On open flower Red-Purple Group N66B. No change in the general tonality at the end of the $4^{th}$ day. Afterwards, general tonality is Red-Purple Group N66C.

Petals:

*Petal count.*—Very double. Approximately 45–55 petals under normal conditions.

*Petal reflex.*—Petals reflex.

*Petal edge.*—Variable. Generally entire, however some notched and some with a point.

*Petal shape.*—Apex shape is round. Shape of base is acute.

*Petal size.*—25–30 mm long; 20–30 mm wide.

*Thickness.*—Average.

*Petal arrangement.*—Generally in a regular pattern with overlapping edges.

*Petaloids.*—Present. Average of 8–12 per flower. Petaloids are 6–8 mm long and 3–4 mm wide. Color of inner side is Red-Purple Group N66B. Color of outer side is Red-Purple Group 67A. Surface texture is smooth. Shape is linear to elliptic.

Reproductive organs:

*Pistils.*—Approximately 40–45 present. Stigmas: Location: Similar in position to anthers. Color: Green-Yellow Group 1A. Styles: Length: 10 mm long. Color: Green-Yellow Group 1A.

*Stamens.*—Approximately 40–45 in number. Anthers: Size: 1.5 mm long. Color: Yellow-Orange Group 14C. Quantity: Approximately 40. Pollen: Limited amounts present. Color: Brown Group 200D. Filaments: Color: Green-White Group 157B. Length: 8 mm. Quantity: Approximately 40–45.

THE PLANT

Plant growth: Vigorous. Upright climbing habit. When grown as a budded nursery plant the average plant height is 250 cm and the average plant width is 100 cm.

Stems:

*Stem color.*—Young wood: Green Group 138A. Older wood: Green Group 138A.

*Stem surface.*—Young wood: Smooth. Older wood: Smooth, with some ridges.

Prickles: Present.

*Incidence.*—5 per 10 cm of stem.

*Size.*—Average length: 4–6 mm.

*Color.*—Immature to mature prickles Greyed-Red Group 179A, with some expressing intonations of Greyed-Purple Group 183A. Prickles senescing to Greyed-Orange Group 177D.

*Shape.*—Deeply concave.

Leaves and leaflets: Normally 7 leaflets on normal leaves in middle of the stem.

*Leaflet shape.*—Ovate; Apex shape is acute; Base shape is obtuse.

*Leaf size.*—110 mm (l)×60–70 mm (w).

*Quantity.*—Abundant.

*Texture.*—Glossy.

*Color, mature foliage.*—Upper Leaf Surface: Green Group 139A. Lower Leaf Surface: Green Group 138A.

*Color, juvenile foliage.*—Upper Leaf Surface: Green Group 139A. Lower Leaf Surface: Green Group 138A.

*Anthocyanin intonation.*—Present. Limited intonations of Greyed-Purple Group 183D present on developing leaves and stems.

Stipules:

*Size.*—10–12 mm (l) — 5–6 mm (w).

*Stipule color.*—Green Group 139A.

*Presence of stipitate glands.*—Present on margins.

*Margins.*—Bearded. Margins serrated.

Petiole:

*Length.*—10–15 mm.

*Diameter.*—1.5 mm average diameter.

*Petiole color.*—Green Group 138A.

*Underneath.*—Smooth, with a few small prickles.

*Stipitate glands.*—Limited numbers present on margins.

Petiole rachis:

*Color.*—Green Group 138A.

*Underneath.*—Smooth, with a few small prickles.

*Stipitate glands.*—Limited numbers present on margins.

Leaflets:

*Size.*—Average size of the terminal leaflet is 35–40 mm(l)×25 mm(w).

*Shape.*—Ovate.

*Margins.*—Serrated.

*Texture.*—Glossy. Leathery.

Hips/seed formation: None observed.

Winter hardiness observation: To date, the new variety has been grown successfully in Zone 5.

Disease resistance: Very good resistance to black spot, powdery mildew, and rust under normal growing conditions.

I claim:

1. A new and distinct variety of rose plant characterized by the following combination of characteristics:

(a) forms abundant, attractive pink flowers;

(b) exhibits upright and climbing growth habit;

(c) propagates well using traditional methods, and;

(d) is resistant to most diseases in the landscape;

substantially as herein illustrated and described.

* * * * *

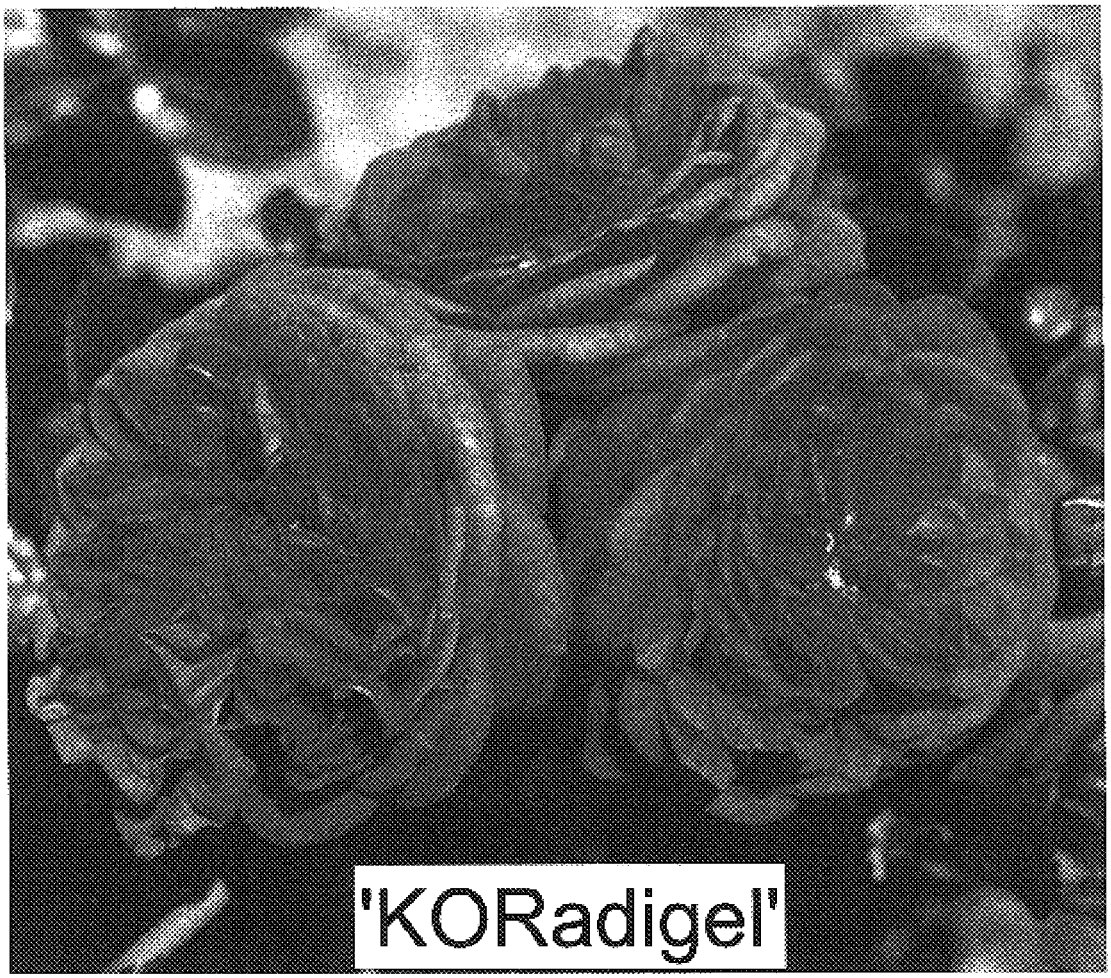
'KORadigel'